United States Patent [19]

Porcelli

[11] 4,302,611
[45] Nov. 24, 1981

[54] PREPARATION OF ACETALDEHYDE

[75] Inventor: Richard V. Porcelli, Yonkers, N.Y.

[73] Assignee: Halcon Research & Development Corp., New York, N.Y.

[21] Appl. No.: 187,691

[22] Filed: Sep. 16, 1980

Related U.S. Application Data

[63] Continuation-in-part of Ser. No. 974,290, Dec. 29, 1978, abandoned.

[51] Int. Cl.³ .................... C07C 47/06; C07C 45/49
[52] U.S. Cl. .................................. 568/484; 568/485; 568/489
[58] Field of Search ............... 568/487, 489, 484, 485

[56] References Cited

U.S. PATENT DOCUMENTS

| 2,727,902 | 12/1955 | Reppe et al. | 568/487 |
| 3,285,948 | 11/1966 | Butter | 568/487 |
| 3,356,734 | 12/1967 | Kuraishi et al. | 568/485 |
| 3,752,859 | 8/1973 | Shell | 568/487 |
| 4,225,517 | 9/1980 | Gane | 568/487 |
| 4,239,704 | 12/1980 | Pretzer et al. | 568/487 |

FOREIGN PATENT DOCUMENTS 48-2525  1/1973  Japan .................................. 568/487

*Primary Examiner*—Werren B. Lone
*Attorney, Agent, or Firm*—William C. Long; David Dick; Riggs T. Stewart

[57] ABSTRACT

Acetaldehyde is prepared by reacting methyl acetate and/or dimethyl ether with carbon monoxide and hydrogen in the presence of a palladium catalyst and an iodine moiety in a reaction zone wherein the reaction mixture is in a continuous boiling state.

6 Claims, No Drawings

PREPARATION OF ACETALDEHYDE

REFERENCE TO RELATED APPLICATION

This is a continuation-in-part of co-pending application Ser. No. 974,290 filed Dec. 29, 1978, now abandoned, for "Preparation of Acetaldehyde."

This invention relates to the preparation of acetaldehyde and is more particularly concerned with the preparation of acetaldehyde by carbonylation procedures.

Acetaldehyde is a well-known chemical of commerce, used primarily as an intermediate in the production of organic chemicals, and has been produced commercially for many years, for example by the hydration of acetylene and the catalytic oxidation of ethyl alcohol, ethylene and saturated hydrocarbons such as butane. More recently, however, it has been discovered that acetaldehyde can be produced by the action of carbon monoxide and hydrogen upon alcohols, ethers and esters in the presence of catalysts based on metals of the 8th Group of the Periodic Table. Such reactions are described, for example, in Reppe et al. U.S. Pat. No. 2,727,902, Butter U.S. Pat. No. 3,285,948, Kuraishi et al. U.S. Pat. No. 3,356,734, and Japanese patent publication 48-19286 and require the use of very high superatmospheric pressures. Belgian Pat. No. 839,321, which is the counter-part of U.S. application Ser. No. 654,662 filed Feb. 5, 1976, discloses the preparation of acetaldehyde as a by-product in the manufacture of ethylidene diacetate by reacting carbon monoxide and hydrogen with methyl acetate at moderate superatmospheric pressures. The selectivity to acetaldehyde described in these publications is, however, in general relatively low and this is obviously a disadvantage when acetaldehyde is the desired product.

It is, therefore, an object of this invention to provide a carbonylation process for the preparation of acetaldehyde in which the selectivity to acetaldehyde is significantly increased and in which the reaction can be carried out at moderately elevated pressures.

In accordance with this invention, this and other objects are realized by continuously carbonylating ($CO+H_2$) methyl acetate and/or dimethyl ether in the presence of a palladium catalyst and an iodine moiety in a boiling reaction zone. A boiling reaction zone is one which is operated under temperature and pressure conditions such that the liquid present is continuously boiling, i.e., is being continuously vaporized and the reaction product effluent is removed from the reaction zone in the vapor state as distinguished from conventional liquid phase reactions wherein the product effluent is withdrawn as a liquid stream. The boiling reaction zone is also distinguished from a vapor-phase zone wherein the reactants and the reaction products are essentially all in the vapor phase at all times. It has been surprisingly discovered that when a palladium catalyst, rather than a catalyst of any other Group VIII metals, is employed, and the reaction is carried out continuously in a boiling reaction zone of the character described, the selectivity to acetaldehyde can approach its theoretical maximum.

The reaction of carbon monoxide and hydrogen upon methyl acetate and dimethyl ether to produce acetaldehyde can be illustrated by the following equations:

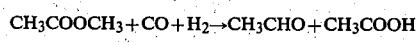

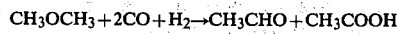

As will be seen from the foregoing equations, one mol of methyl acetate or dimethyl ether will theoretically produce a mol of acetaldehyde and a mol of acetic acid. In accordance with the invention, the formation of other products which tend to reduce the yield of acetaldehyde is minimized so that the quantity of acetaldehyde produced from a unit quantity of methyl acetate or dimethyl ether will more nearly approach the theoretical. At the same time, the amount of methyl acetate or dimethyl ether converted to acetaldehyde and acetic acid is maintained at a desirable level. The term "selectivity" as used herein has its conventional meaning viz.

$$\% \text{ selectivity} = \frac{\text{mols acetaldehyde produced}}{\text{mols methyl acetate reacted}} \times 100$$

as will be seen from the equations set forth above, the theoretical selectivity to acetaldehyde is 100% wherein one mol of acetaldehyde and one mol of acetic acid are produced per mol of methyl acetate or dimethyl ether reacted.

The process of the present invention is related to the process of Belgian Pat. No. 839,321 but the process of this invention is carried out with a selected catalyst under selected conditions, specifically including the use of a boiling reaction zone so that a new result is obtained in that production of acetaldehyde is significantly increased and the formation of products such as acetic anhydride and ethylidene diacetate is reduced.

In the following discussion reference is made to methyl acetate for ease of description but it will be understood that the methyl acetate can be replaced in whole or in part by dimethyl ether. When dimethyl ether is used, it is conveniently supplied to the reactor under pressure in the liquid state.

As in the process of Belgian Pat. No. 839,321, the reaction system necessarily contains a halogen moiety and, in the case of this invention, the halogen moiety is an iodine moiety. The ratio of iodine moiety to methyl acetate in the reaction zone should be in the range of 0.001 to 10 mols per mol. The iodine moiety is preferably supplied in the form of methyl iodide but in a continuous process such as the process of the present invention wherein the methyl iodide in the effluent from the boiling reaction zone is recovered and recycled to the reaction zone, any losses can be made up not only by supplying additional methyl iodide but they can also be made up by supplying the iodine moiety in the form of elemental iodine, hydrogen iodide, acetyl iodide and like sources of the iodine moiety.

It is believed that these forms of the iodine moiety react in the environment of the boiling reaction zone to form methyl iodide.

The ratio of hydrogen to carbon monoxide is also important in the process of this invention and should be between 0.05 and 10 mols per mol, preferably between 0.1 and 5 mols per mol and most perferably between 0.2 and 1 mol per mol.

Only moderately elevated pressures are needed in carrying out the process of this invention, as distinguished from the highly-elevated pressures required by the previously-disclosed processes directed to the preparation of acetaldehyde and, in general, hydrogen and carbon monoxide partial pressures employed will each lie within the range of 25 to 2000 psi, preferably between 50 and 1000 psi and most preferably between 50 and 500 psi. The total pressure of the reaction system will ordinarily not exceed 2000 psig but obviously it will be high as is necessary to provide the desired hydrogen and carbon monoxide partial pressures.

The hydrogen and carbon monoxide are suitably fed into the liquid reaction medium so that they pass upwardly through it. This not only provides agitation but facilitates control of the partial pressures of these two gases. The rate of flow can vary widely but is typically 1 to 500 mols per hour per liter of liquid reaction medium, preferably 5 to 100 mols per hour per liter, most perferably 10 to 75 mols per hour per liter.

The temperature of the reaction mixture is selected to keep the reaction mixture under continuously boiling conditions, i.e., to maintain continuous vaporization of the liquid reaction mixture, at the total pressure and total gas flow rate employed. Ordinarily, the temperature will lie within the range of 100° and 200° C.

Reaction time is not a significant parameter of the process of this invention, depending to a large extent upon the temperature employed as well as upon reactant concentrations. Suitable reaction or "residence" times would normally be within the range of 0.1 to 8 hours. The reaction is carried out under substantially anhydrous conditions.

The hydrogen and the carbon monoxide are each preferably employed in substantially pure form, as available commercially. Inert diluents such as carbon dioxide, nitrogen, methane, and/or inert gases (e.g., helium, argon, neon, etc.) can be present if desired. The presence of inert diluents of these types does not affect the desired carbonylation reactions, but their presence makes it necessary to increase the total pressure in order to maintain the desired carbon monoxide and hydrogen partial pressures. Similarly, the presence of conventional organic impurities found in commercial grades of methyl acetate and methyl iodide pose no problem to the practice of this invention.

All feed components (i.e., carbon monoxide, hydrogen, as well as the methyl acetate and methyl iodide) should be substantially free from water since, in this fashion, the maintenance of a substantially anhydrous condition within the reaction zone is facilitated. The presence of minor amounts of water, however, such as may be found in these commercially available reactants, is permissible. Normally, however, the presence of more than 5 mol % of water in any one or more of the reactants should be avoided, and the presence of less than 1.0 mol % of water is preferred, with essentially no water being the most desirable. The palladium catalyst can be employed in an convenient form, viz., in the zero valent state or in any higher valent form. For example, the catalyst to be added can be the metal itself, in finely divided form, or it can be added as a carbonate, oxide, hydroxide, nitrate, bromide, iodide, chloride, lower alkoxide (i.e., $C_1$-$C_5$, such as the methoxide or ethoxide), phenoxide, or metal carboxylate wherein the carboxylate ion is derived from an alkanoic acid of 1 to 20 carbon atoms. Similarly, complexes of the metals can be employed, for example, the metal carbonyls, such as the palladium carbonyls, or as other complexes such as the carbonyl halides, or as the acetylacetonates. Illustrative specific forms in which the palladium catalyst can be added to the system include palladium monoxide, palladium acetate, palladium chloride, palladium bromide, palladium iodide, palladium hydride, palladium metal, and the like.

The palladium catalyst can be employed in forms initially or eventually soluble in the liquid-phase reaction medium to provide a homogeneous catalyst system. Alternatively, insoluble (or only partially soluble) forms, providing a heterogeneous catalyst system, can be employed. Amounts of palladium catalyst (calculated as contained noble metal based upon the total quantity of liquid-phase reaction medium) of as little as about $1 \times 10^{-4}$ wt. % (1 ppm) are effective, although normally amounts of at least 10 ppm, desirably at least 100 ppm, and preferably at least 1000 ppm would be employed. Upper concentration limits on carbonylation catalyst quantity appears to be controlled more by economics than by any advantage in either rate or selectivity that can be observed. Economic considerations would normally suggest that more than 10 wt. % contained noble metal would not normally be employed.

The effectiveness of the palladium catalyst is enhanced, particularly with respect to the reaction rate and concentration of the desired product by the concurrent use of organic promoters capable of forming a coordination compound with the Group VIII noble metal catalyst. Suitable organic promoters are organic non-hydrocarbon materials containing within their molecular structure one or more electron rich atoms possessing one or more pairs of electrons available for formation of coordinate bonds with the noble metal catalyst. Most such organic promoters can be characterized as Lewis bases for the particular anhydrous reaction system involved. Enhancement of catalyst performance is also obtained by the use of inorganic (primarily metallic) promoters in addition to the organic promoters. Suitable metallic promoters include elements and/or compounds of elements having atomic weights greater than 5 of Groups IA, IIA, IIIA, IVB, VIB, and the non-noble metals of Groups VIII, and the metals of the lanthanide and actinide groups of the Periodic Table as set forth in the *Handbook of Chemistry and Physics*, 42nd Ed., Chemical Rubber Publishing Co., Cleveland, Ohio (1960) at pages 448–449. Preferred inorganic promoters include the metals of Groups VIB and the non-noble metals of Group VIII, especially chromium, iron, cobalt, and nickel and most preferably chromium.

Such promoters can be introduced concurrently with the reactants to the reaction zone or can be incorporated together with the Group VIII noble metal by formation of ligand complexes with the noble metal prior to introduction of the noble metal-ligand complex to the reaction zone. When pre-formed ligand complexes are used, concurrent use of promoters (either organic or inorganic) is not necessary, though of course such can be employed if desired.

Typical organic promoters are organo-nitrogen and organo-phosphorus-containing compounds, organo-stibines and organo-arsines. Preferred are the organo-nitrogen and organo-phosphorus compounds, especially the organo-phosphines.

Suitable nitrogen-containing organic promoters include, by way of illustration, pyrrole, pyrrolidine, pyridine, piperidine, pyrimidine, the picolines, pyrazine (and their N-lower-alkyl-substituted derivatives, lower alkyl meaning $C_1$-$C_5$ such as N-methyl pyrrolidine), benzotriazole; N,N,N',N'-tetramethylethylenediamine, N,N,N',N'-tetraethylethylenediamine, N,N,N'-N'-tetra-n-propylethylenediamine, N,N,N',N'-tetramethylmethylenediamine, N,N,N',N'-tetraethylmethylenediamine, N,N,N',N'-tetraisobutylmethylenediamine, piperazine, N-methylpiperazine, N-ethylpiperazine, 2-methyl-N-methylpiperazine 2,2'-dipyridyl, methyl-substituted 2,2'-dipyridyl, ethyl-substituted 2,2'-dipyridyl, 1,4-diazabicyclo [2.2.2]octane, methyl-substituted 1,4-diazabicylo[2.2.2]octane, purine, 2-aminopyridine, 2-(dimethylamino)pyridine, 1,10-phenanthroline, methyl-substituted 1,10-phenanthroline, 2-(dimethylamino)-6-methoxyquinoline, 7-chloro-1,10-phenanthroline, 4-triethylsilyl-2,2'-dipyridyl, 5-(thiapentyl)-1,10-phenanthroline, tri-n-butyl-amine, and the like.

Suitable organic promoters containing both oxygen and nitrogen atoms are ethanolamine, diethanolamine, isopropanolamine, di-n-propanolamine, N,N-dimethylglycine, N,N-diethylglycine, 1-methyl-2-pyrrolidinone, 4-methylmorpholine, N,N,N',N'-tetramethylurea, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl)iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Suitable stibines and arsines are exemplified by the following illustrative materials: trimethyl arsine, triethyl arsine, triisopropyl stibine, ethyldiisopropyl stibine, tricyclohexyl arsine, triphenyl stibine, tri(o-tolyl)-stibine, phenyldiisopropyl arsine, phenyl diamyl stibine, diphenylethylarsine, tris(diethylaminomethyl) stibine, ethylene bis(diphenyl arsine), hexamethylene bis(diisopropyl arsine) pentamethylene bis(diethylstibine) etc.

Desirable organic promoters are the organo nitrogen or organo phosphorus compounds wherein the nitrogen or phosphorus atoms are, at least in part, trivalent. Many of these preferred compounds may also contain oxygen atoms such as, for example, 1-methyl-2-pyrrolidinone and N,N,N',N'-tetramethylurea. Illustrative are the tertiary amines of the formula:

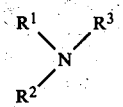

wherein $R^1$, $R^2$, and $R^3$ are the same or different and are alkyl, cycloalkyl, or aryl radicals, each preferably having not more than about 10 carbon atoms. Also advantageously used are the heterocyclic amines of the pyridine type such as pyridine itself, the picolines, quinoline, and methyl quinoline. The tertiary phosphines of the following formula:

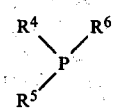

wherein $R^4$, $R^5$, and $R^6$ have the same meaning as $R^1$, $R^2$, and $R^3$, respectively, are most especially preferred. Exemplary of particularly suitably phosphines include trimethyl phosphine, tri-t-butyl phosphine, tri-n-butyl phosphine, tricyclohexyl phosphine, and triphenyl phosphine.

The quantity of organic promoter employed is related to the quantity of palladium catalyst within the reaction zone. Normally the quantity is such that at least 0.5, desirably at least 1, and preferably at least 2 mols of promoter compound per mol of palladium is present in the reaction zone. Little advantage is observed, on the other hand, when large excesses of organic promotor per mol of palladium catalyst are employed. Normally, therefore, operation with more than 30 mols of promoter per mol of palladium catalyst in the reaction zone would not be employed. Particularly advantageous results can be obtained when the number of mols of organic promoter per mol of palladium catalyst within the boiling reaction zone is between 4 and 16 mol per mol, and preferably between 6 to 10 mol per mol.

The foregoing ratios of organic promoter to palladium of course assume that the promoter and palladium catalyst are introduced to the reaction zone as distinct species. When, as also indicated to be practicable, preformed organic promoter-palladium ligand complexes are employed, the amount of promoter is, of course, dictated by the stoichiometry of the complex. Additional promoter can then be added to the reaction zone during the course of the reaction, either periodically or continuously, to assist in maintenance of the stability of the complex, if desired.

An additional type of organically promoted palladium catalysts of utility as carbonylation catalysts for the process of this invention are those in which the palladium catalyst metal is chemically bonded to a polymeric substrate which can be organic or inorganic. Such metal-polymer complexes are clearly heterogeneous in the physical sense because insoluble; however, they display chemical characteristics more nearly akin to homogeneous than to heterogeneous catalysts. Such metal-polymer complexes and procedures for their preparation are known; see Michalska, Z. M. and Webster, D. E. "Supported Homogeneous Catalysts," CHEMTECH, Feb. 1975, pages 117–122 and references cited therein. Those complexes particularly suitable for use in this invention comprise noble metal bonded to a silica, polyvinyl chloride or cross-linked polystyrene-divinylbenzene substrate by phosphine, silyl, amine, or sulfide linkages.

Effective inorganic promoters include the elements (and compounds of elements) having atomic weights greater than 5 of Groups IA, IIA, IIIA, IVB, VIB, the non-noble metals of Group VIII, and the metals of the lanthanide and actinide groups of the Periodic Table. Particularly preferred are the lower atomic weight metals of each of these groups, e.g., those having atomic weights lower than 100, and especially preferred are the metals of Group VIB and the non-noble metals of Group VIII. In general, the most preferred elements are lithium, magnesium, calcium, titanium, chromium, iron, cobalt, nickel, and aluminum. Most preferred are lithium, chromium, cobalt, iron and nickel, especially chromium.

The inorganic promoters can be used in their elemental form, e.g., as finely divided or powdered metals, or they can be employed as compounds of various types, both organic and inorganic, which are effective to introduce the element as the cation into the reaction system under reaction conditions. Thus, typical compounds of the promoter elements include oxides, hydroxides, halides (preferably bromides and iodides), oxyhalides, hydrides, carbonyls, alkoxides, nitrates, nitrites, phosphates, phosphites, and the like. Especially preferred organic compounds are the salts of organic aliphatic, cycloaliphatic, naphthenic and araliphatic monocarboxylic acids, e.g. alkanoates such as the acetates, butyrates, decanoates, laurates, stearates, benzoates, and the like. Other suitable compounds include the metal alkyls as well as chelates, associate compounds and enol salts. Particularly preferred are the elemental forms, compounds which are bromides and iodides and organic acid salts, preferably acetates. Mixtures of inorganic promoters can be used if desired, especially mixtures of elements from different groups of the Periodic Table. Of course, it is also practicable, and sometimes advantageous, to use both organic and inorganic promoters in conjunction with the palladium catalyst.

The quantity of inorganic promoter can vary widely, but is in general used in the amounts specified above for the organic promoters.

The boiling reaction zone is suitably provided by a pressure vessel equipped with an inlet for methyl acetate and recycled liquid materials, such as methyl iodide, and an inlet for hydrogen and carbon monoxide, including recycled streams of these gases. As mentioned above, the gaseous feed to the reaction zone is suitably introduced into the lower portion of the zone so that the gases pass upwardly through the boiling reaction medium and serve to agitate it. It will be understood that the essentially non-volatile palladium catalyst will remain at all times in the reaction zone as a component of the boiling liquid body and that the only effluent from the reaction zone in the vapor phase will consist not only of the non-condensible hydrogen and carbon monoxide but also of the volatized organic compounds, primarily acetaldehyde, acetic acid, ethylidene diacetate, acetone, acetic anhydride, methyl acetate, and methyl iodide. This vaporous effluent, after it has been removed from the boiling reaction zone, is cooled in one or more stages to condense its condensible components, and the non-condensible components are recycled, suitably after appropriate compression, to the reaction zone along with fresh hydrogen and carbon monoxide. A purge of the recycled gases may be taken in order to prevent the buildup of contaminating gases which may have been present in the original feed or may have been formed in the reaction zone as will be apparent to persons skilled in the art. The condensate from such cooling which consists of the organic products produced in the reaction, methyl iodide and unreacted methyl acetate is then subjected to fractional distillation in order to separate the desired acetaldehyde and in order to separate the relatively volatile methyl iodide and methyl acetate for recycling to the boiling reaction zone. The remaining components of the condensed reaction mixture can be separated as desired to cover the individual compounds by further fractional distillation. If it is desired to recover possibly present by-product acetone in pure form, a particularly effective method for doing so is disclosed in the application of Robert Hoch, James Leacock and Chee-Gen Wan entitled Recovery of Acetone Produced by Carbonylation, Ser. No. 974,291, filed Dec. 29, 1978 now U.S. Pat. No. 4,252,748. The disclosure of that application is incorporated herein by reference.

The following examples of specific application will serve to provide a fuller understanding of the invention but it will be understood that these examples are given for illustrative purposes only and are not to be interpreted as limitative of the invention.

EXAMPLE 1

Using a reactor in the form of a 1-liter autoclave provided with an inlet for liquid feed, an inlet for gaseous feed connected to a sparger at the bottom of the reactor, and an outlet line connected to a condenser effective to condense substantially all of the components of the reactor effluent having boiling points above 0° C., acetaldehyde is produced from methyl acetate in the presence of carbon monoxide and hydrogen and in the presence of a catalyst composed of palladium and tributyl phosphine, as follows. The reactor is charged with approximately 0.67 liter of a mixture of 20 wt. % of methyl iodide and 80 wt. % of methyl acetate to which has been added approximately 14 grams of palladium as palladium acetate and 217 grams of tributyl phosphine and then heated for 30 mins. at 160° C. under a partial pressure of carbon monoxide of approximately 300 psi, and of hydrogen of 100 psi. Continuous operation is then begun with a feed of 69 grams per hour of methyl iodide and 268 grams per hour of methyl acetate. Carbon monoxide and hydrogen are supplied to the reactor at this time to maintain a continuous carbon monoxide partial pressure of about 390 psi and a continuous hydrogen partial pressure of about 63 psi (total pressure 565 psia). The hydrogen and the carbon monoxide (approximate molar ratio of 0.16 to 1) are continuously introduced through the sparger into the lower portion of the liquid body in the reactor which is at a temperature of 160° C. and is continuously boiling. The combined hydrogen and carbon monoxide are introduced at a rate of approximately 16 mols per hour. The carbon monoxide and hydrogen feed is composed of carbon monoxide and hydrogen in the recycled gas which is separated from the reactor effluent, as will be described below, plus fresh hydrogen and carbon monoxide in amounts to provide the specified partial pressures. The vapors present in the boiling reaction zone are continuously removed at the rate of 22 mols per hour including non-condensible gases. The residence time is about 2.4 hours. The removed vaporous effluent is condensed to separate the components having boiling points above 0° C. and to leave a gaseous mixture composed primarily of carbon monoxide and hydrogen with very small amounts of by-product gases such as carbon dioxide, ethylene and methane, along with trace amounts of condensible components not completely separated in the condensation step. This gaseous stream is then recycled to the boiling reaction zone after a purge of about 4.3 mols per hour is taken to prevent build-up of the by-product gases. The condensed portion of the vaporous reactor effluent is composed primarily of acetaldehyde, acetic acid, methyl iodide and unreacted methyl acetate. This mixture is separated by fractional distillation, the methyl acetate and the methyl iodide being recycled to the reactor in combination with fresh methyl acetate and make-up iodide to provide the above-described liquid feed. It is found that the reaction provides a conversion based on methyl acetate of about 25 mol percent and that the selectivity to acetaldehyde is 81% of the theoretical.

EXAMPLE 2

Example 1 is repeated in a series of additional runs which are carried out as described in Example 1 except that the partial pressure of hydrogen is varied from 56 psi to 127 psi (the partial pressure of carbon monoxide varying only slightly from 380 psi to 406 psi), the total pressure is varied from 535 psia to 615 psia, the weight ratio of methyl acetate to methyl iodide is varied from 1:1 to 4:1 and the feed rate to the reactor is varied from 156 grams per hour to 580 grams per hour. The concentration of palladium catalyst and the concentration of tributyl phosphine are maintained at the same values used in Example 1, i.e., approximately 0.2 and 0.8 mol per liter, respectively. The selectivity to acetaldehyde is found to range from 76% to 83% with an average value of 80%.

COMPARATIVE EXAMPLE A

In this example, a reaction comparable to that described in Example 1 is carried out except that the reaction is conducted under non-boiling conditions in the liquid phase and the effluent from the reaction zone is the liquid reaction mixture which is then subjected to flash distillation to remove the volatile components, and the residual material from that distillation is continuously recycled to the reaction zone.

Thus, using a reactor in the form of a 1-gallon stirred autoclave provided with an inlet for liquid feed, and a line connected to a source of carbon monoxide and a source of hydrogen, methyl acetate is carbonylated in the presence of a catalyst composed of rhodium trichloride trihydrate, tributyl phosphine and chromium hexacarbonyl, as follows. The reactor is charged with approximately 23 liters of a mixture of 20 wt. % of methyl iodide and 80 wt. % of methyl acetate containing approximately 48 grams palladium as palladium acetate and 685 grams of tributyl phosphine and then heated for one hour at 160° C. under a partial pressure of carbon monoxide of approximately 300 psi, and of hydrogen of 50 psi. Continuous operation is then begun with a feed of 230 grams/hr. of methyl iodide and 980 grams/hr. of methyl acetate. Carbon monoxide and hydrogen are supplied to the reactor at this time to maintain a continuous carbon monoxide partial pressure of about 403 psi and a continuous hydrogen partial pressure of about 52 psi (total pressure 600 psi). The liquid reaction mixture is continuously withdrawn from the reactor at the rate of 3700 grams/hr. and passes to a flash distillation chamber maintained under a pressure of 50 psig and a temperature of 135°–140° C. Approximately 1200 grams/hr. of the liquid effluent from the carbonylation reactor is volatilized, and about 2500 grams per hour of non-volatilized liquid containing the catalyst components is recycled to the reactor. Under these conditions it is found that the conversion based on methyl acetate is about 19% and the selectivity to acetaldehyde is about 58%.

COMPARATIVE EXAMPLE B

Comparative Example A is repeated in a series of additional runs which are carried out as described in Example A except that the hydrogen partial pressure is varied from 54 psi to about 100 psi, the carbon monoxide partial pressure is varied from 360 to about 380, and the feed rate is varied from 414 grams per hour to 797 grams per hour. The ratio of methyl acetate to methyl iodide and the concentrations of palladium catalyst and tributyl phosphine are the same as used in Comparative Example A, i.e., approximately 0.2 mol per liter of palladium catalyst to 0.8 mol per liter of tributyl phosphine. The selectivity to acetaldehyde is found to range from 49% to 68% with an average of 58%.

What is claimed is:

1. A process for the preparation of acetaldehyde which comprises continuously reacting methyl acetate and/or dimethyl ether with carbon monoxide and hydrogen in a reaction zone containing a palladium catalyst and an iodine moiety at a temperature of at least about 100° C. and under a pressure of at least about 25 psig, the liquid reaction mixture being maintained under continuous boiling conditions, whereby a vaporous reaction product mixture is produced from the boiling liquid reaction mixture, and continuously removing said vaporous mixture from said reaction zone.

2. A process as defined in claim 1, wherein the ratio of hydrogen to carbon monoxide is in the range of 0.05 to 10 mols of hydrogen per mol of carbon monoxide.

3. A process as defined in claim 2, wherein the partial pressures of said hydrogen and said carbon monoxide are each at least about 50 psi.

4. A process for the preparation of acetaldehyde which comprises continuously reacting methyl acetate with carbon monoxide and hydrogen in a reaction zone containing a palladium catalyst and an iodine moiety at a temperature of at least about 100° C. and under a pressure of at least about 25 psig, the liquid reaction mixture being maintained under continuous boiling conditions, whereby a vaporous reaction product mixture is produced from the boiling liquid reaction mixture, and continuously removing said vaporous mixture from said reaction zone.

5. A process as defined in claim 4, wherein the ratio of hydrogen to carbon monoxide is in the range of 0.05 to 10 mols of hydrogen per mol of carbon monoxide.

6. A process as defined in claim 5, wherein the partial pressures of said hydrogen and said carbon monoxide are each at least about 50 psi.

* * * * *